United States Patent [19]

Takasugi et al.

[11] Patent Number: 4,931,453
[45] Date of Patent: Jun. 5, 1990

[54] DI PHENYLPYRIDAZINE COMPOUNDS, PROCESSES FOR THE PREPARATION THEREOF AND PHARMACEUTICAL COMPOSITIONS COMPRISING THE SAME

[75] Inventors: Hisashi Takasugi; Atsushi Kuno, both of Osaka; Hiroyoshi Sakai, Kyoto; Yoshie Sugiyama, Hyogo; Takao Takaya, Kawanishi, all of Japan

[73] Assignee: Fujisawa Pharmaceutical Company, Ltd., Osaka, Japan

[21] Appl. No.: 286,169

[22] Filed: Dec. 19, 1988

Related U.S. Application Data

[62] Division of Ser. No. 940,923, Dec. 12, 1986, Pat. No. 4,831,030.

[30] Foreign Application Priority Data

Dec. 12, 1985 [GB] United Kingdom ................ 8530602

[51] Int. Cl.$^5$ .................... A61K 31/50; C07D 403/06; C07D 403/12
[52] U.S. Cl. ..................................... 514/252; 544/238
[58] Field of Search ..................... 514/252; 544/238

[56] References Cited

U.S. PATENT DOCUMENTS

| | | | |
|---|---|---|---|
| 4,280,998 | 7/1981 | Franckowiak et al. | 514/252 |
| 4,348,395 | 9/1982 | Franckowiak et al. | 544/238 |
| 4,360,520 | 11/1982 | Meyer et al. | 514/252 |
| 4,727,073 | 2/1988 | Takaya et al. | 514/252 |
| 4,831,030 | 5/1989 | Takasugi et al. | 514/252 |
| 4,857,527 | 8/1989 | Takaya et al. | 514/237.2 |

Primary Examiner—Nicholas S. Rizzo
Assistant Examiner—E. Bernhardt
Attorney, Agent, or Firm—Oblon, Spivak, McClelland, Maier & Neustadt

[57] ABSTRACT

The invention relates to diphenylpyridazine compounds useful in the treatment of cerebrovascular disease, of the formula:

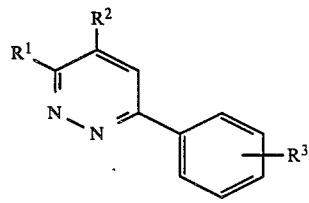

wherein $R^1$ is piperazinyl(lower)alkyl, carbamoyl substituted with piperazinyl(lower)alkyl, or piperazinylcarbonyl, in each of which a piperazinyl group may be substituted with lower alkyl,
$R^2$ is phenyl substituted with nitro, and
$R^3$ is hydrogen or halogen, or a pharmaceutically acceptable salt thereof.

6 Claims, No Drawings

DI PHENYLPYRIDAZINE COMPOUNDS, PROCESSES FOR THE PREPARATION THEREOF AND PHARMACEUTICAL COMPOSITIONS COMPRISING THE SAME

This is a division of application Ser. No. 06/940,923, filed Dec. 12, 1986, now U.S. Pat. No. 4,831,030.

This invention relates to new N-containing heterocyclic compounds. More particularly, this invention relates to new N-containing heterocyclic compounds and their salts which are useful in the treatment of hypertension, cardiovascular and cerebrovascular diseases in human beings and animals, to processes for the preparation thereof and no pharmaceutical compositions comprising the same as an active ingredient.

The N-containing heterocyclic compounds of this invention are represented by the following general formula [I]:

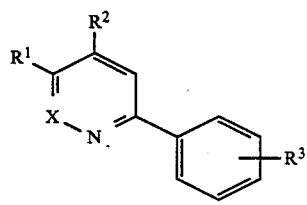

wherein
$R^1$ is lower alkyl optionally substituted with hydroxy, halogen or a heterocyclic group, carboxy, esterified carboxy, carbamoyl optionally substituted with heterocylic(lower)alkyl or lower alkylamino(lower)alkyl, N-containing heterocycliccarbonyl optionally substituted with lower alkyl, or ureido optionally substituted with lower alkylamino(lower)alkyl, and $R^3$ is hydrogen or halogen;
$R^2$ is phenyl substituted with nitro, and
X is =N— or

in which $R^4$ is lower alkyl or halo(lower)alkyl, or is taken together with $R^1$ to form an N-containing heterocyclic group optionally substituted with oxo and lower alkylamino(lower)alkyl; or $R^2$ is lower alkyl, and X is

in which $R^4$ is phenyl substituted with nitro.

The object compound [I] or its salt can be prepared by processes as illustrated in the following reaction schemes.

Process 1

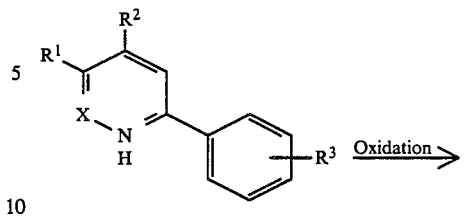

[II] or its salt

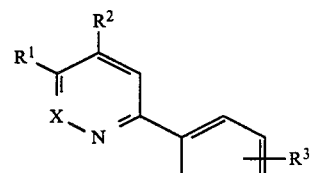

[I] or its salt

Process 2

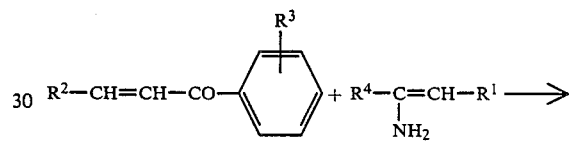

[III]    [IV] or its salt

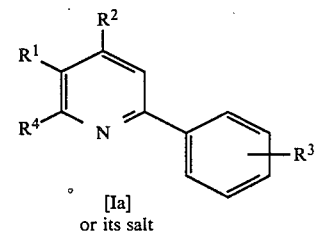

[Ia] or its salt

Process 3

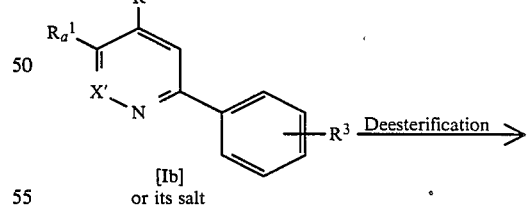

[Ib] or its salt

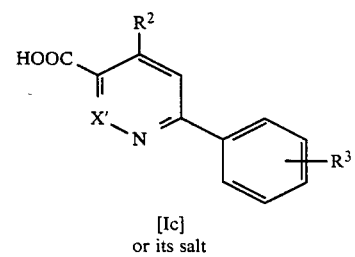

[Ic] or its salt

Process 4

-continued
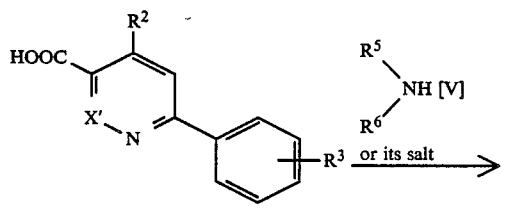
[Ic]
or its reactive
derivative at the
carboxy group or
a salt thereof
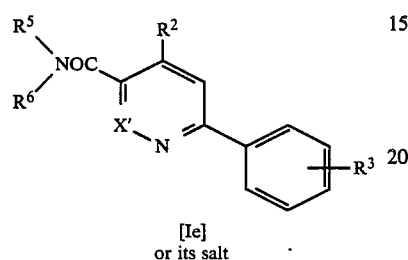
[Ie]
or its salt
Process 5
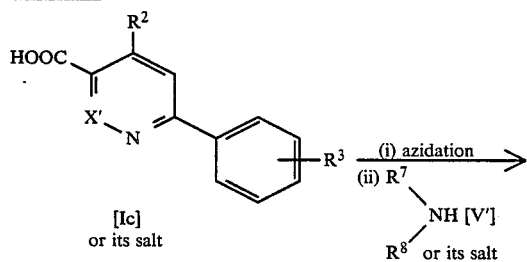
[Ic]
or its salt
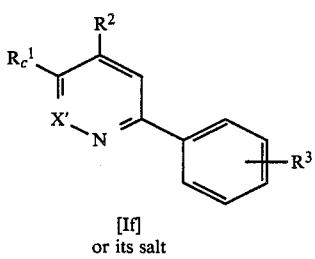
[If]
or its salt
Process 6
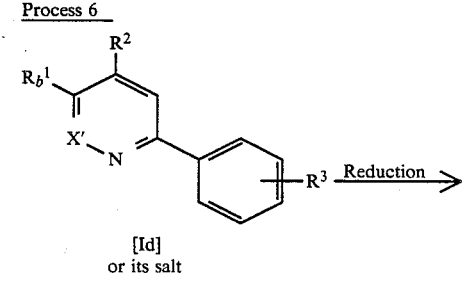
[Id]
or its salt
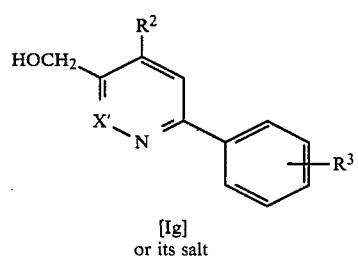
[Ig]
or its salt
Process 7
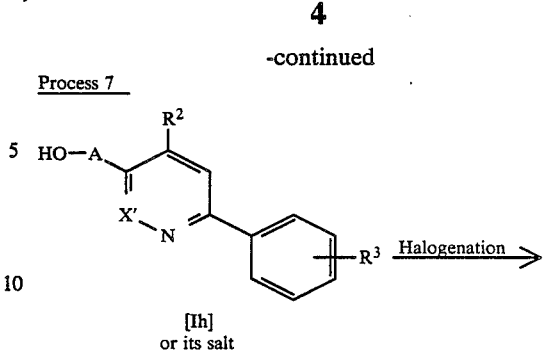
[Ih]
or its salt
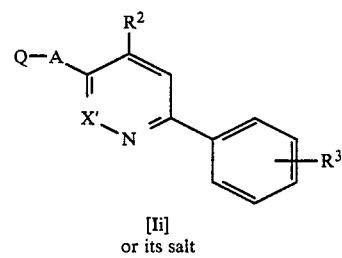
[Ii]
or its salt
Process 8
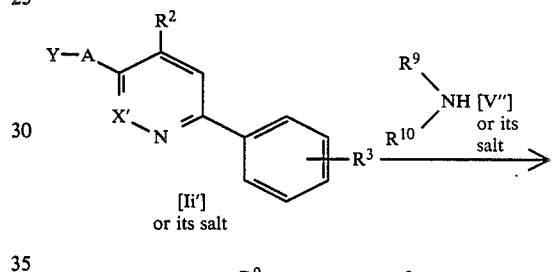
[Ii′]
or its salt
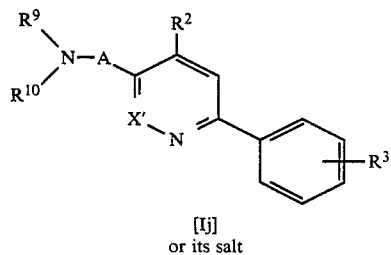
[Ij]
or its salt
Process 9
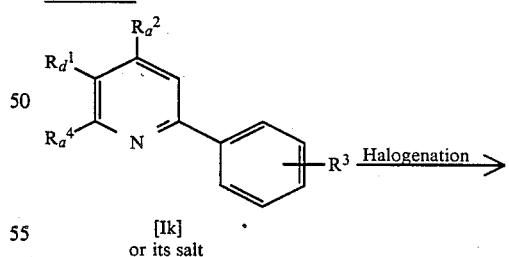
[Ik]
or its salt
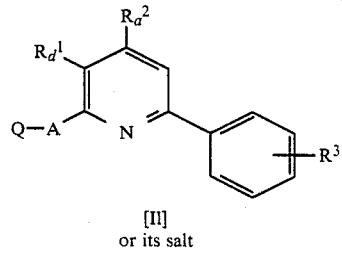
[Il]
or its salt
Process 10

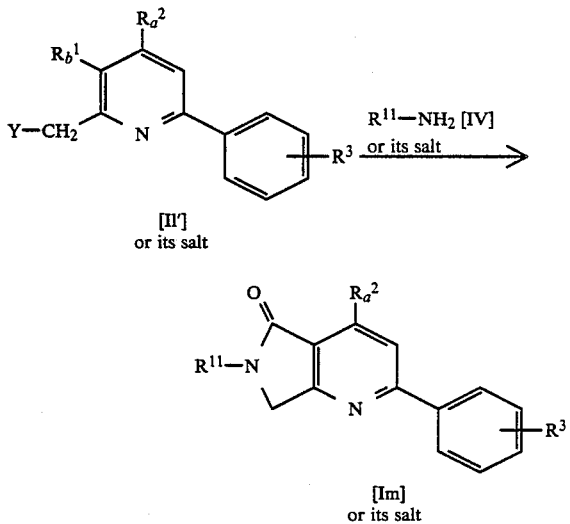

[II']
or its salt

[Im]
or its salt wherein $R^5$ and $R^6$ are each hydrogen, lower alkylamino(lower)alkyl or a heterocyclic(lower)alkyl, or $R^5$ and $R^6$ are taken together with the nitrogen atom to which they attach to form an N-containing heterocyclic group which may be substituted with lower alkyl, $R^7$ and $R^8$ are each hydrogen or lower alkylamino(lower)alkyl, $R^9$ and $R^{10}$ are taken together with the nitrogen atom to which they attach to form a heterocyclic group, $R^{11}$ is lower alkylamino(lower)alkyl, $R^1{}_a$ is esterified carboxy, $R^1{}_b$ is carboxy or esterified carboxy, $R^1{}_c$ is ureido optionally substituted with lower alkylamino(lower)alkyl, $R^1{}_d$ is lower alkyl optionally substituted with hydroxy, halogen or a heterocyclic group, carboxy, esterified carboxy, carbamoyl optionally substituted with heterocyclic(lower)alkyl or lower alkylamino(lower)alkyl, N-containing heterocycliccarbonyl optionally substituted with lower alkyl, or ureido optionally substituted with lower alkylamino(lower)alkyl, $R^2{}_a$ is phenyl substituted with nitro, $R^4{}_a$ is lower alkyl, A is lower alkylene, Q is halogen, X' is =N— or

in which $R^4{}_b$ is lower alkyl, halo(lower)alkyl or phenyl substituted with nitro, Y is a leaving group, and $R^1$, $R^2$, $R^3$, $R^4$ and X are each as defined above.

Particulars of the various definitions mentioned in this specification and preferred examples thereof are explained in the following.

The term "lower" used in this specification is intended to mean a group having 1 to 6 carbon atoms and preferably 1 to 4 carbon atoms, unless otherwise provided.

Suitable "lower alkyl" may be straight or branched one such as methyl, ethyl, propyl, isopropyl, butyl, tert-butyl, pentyl, hexyl or the like.

Preferable examples of "lower alkyl substituted with hydroxy" may be hydroxymethyl, hydroxyethyl, hydroxypropyl or the like.

Suitable "halogen" may be fluorine, chlorine, bromine or iodine.

Preferable examples of "lower alkyl substituted with halogen" may be chloromethyl, difluoromethyl, bromomethyl, 2-chloroethyl, 2-bromoethyl or the like.

Suitable "heterocyclic group" may be saturated 5 or 6 membered N-, or N- and S-, or N- and O-containing heterocyclic group such as piperidyl, piperazinyl, morpholinyl, thiomorpholinyl, pyrrolidinyl, imidazolidinyl, pyrazolidinyl, oxazolidinyl or the like, which may be substituted with aforesaid lower alkyl etc.

Preferable examples of "lower alkyl substituted with a heterocyclic group" may be morpholinomethyl, morpholinoethyl, thiomorpholinomethyl, thiomorpholinoethyl, piperazinylmethyl, methyl substituted piperazinylmethyl, or the like.

Suitable ester moiety in the term "esterified carboxy" may include lower alkyl ester [e.g. methyl ester, ethyl ester, propyl ester, isopropyl ester, butyl ester, tert-butyl ester, pentyl ester, hexyl ester, etc.], mono (or di or tri)halo(lower)alkyl ester [e.g. iodoethyl ester, dichloroethyl ester, trichloroethyl ester, trifluoromethyl ester, etc.], hydroxy(lower)alkyl ester [e.g. hydroxymethyl ester, hydroxyethyl ester, hydroxypropyl ester, hydroxybutyl ester, etc.], ar(lower)alkyl ester [e.g. benzyl ester, 4-nitrobenzyl ester, trityl ester, etc.], alkenyl ester [e.g. vinyl ester, allyl ester, etc.] and the like.

Preferable examples of "esterified carboxy" may be lower alkoxycarbonyl [e.g. methoxycarbonyl, ethoxycarbonyl, propoxycarbonyl, isoproproxycarbonyl, butoxycarbonyl, tert-butoxycarbonyl, pentyloxycarbonyl, hexyloxycarbonyl, etc.] or the like.

Suitable "heterocyclic(lower)alkyl" may be the above-mentioned "lower alkyl substituted with a heterocyclic group", or the like.

Preferable examples of "carbamoyl substituted with heterocyclic(lower)alkyl" may be morpholinomethylcarbamoyl, morpholinoethylcarbamoyl, thiomorpholinomethylcarbamoyl, thiomorpholinoethylcarbamoyl, methyl substituted piperazinylethylcarbamoyl, or the like.

Suitable "lower alkylamino(lower)alkyl group" may be mono(lower alkyl)amino(lower)alkyl [e.g. methylaminomethyl, ethylaminomethyl, isopropylaminomethyl, 2-methylaminomethyl, 3-methylaminopropyl, 3-methylaminobutyl, etc.], di(lower alkyl)amino(lower)alkyl [e.g. dimethylaminomethyl, dimethylaminoethyl, 2-(N-methyl-N-ethylamino)ethyl, etc.] or the like.

Preferable examples of "carbamoyl substituted with lower alkylamino(lower)alkyl" may be N-(methylaminomethyl)-carbamoyl, N-(dimethylaminomethyl)carbamoyl, N-(2-dimethylaminoethyl)carbamoyl, N-(2-diethylaminoethyl)carbamoyl, N-[3-(N-methyl-N-ethylamino)propyl]carbamoyl, or the like.

Suitable "N-containing heterocycliccarbonyl" may be saturated 5 or 6 membered N-, or N- and S-, or N- and O-containing heterocyclic-carbonyl such as 1-pyrrolidinylcarbonyl, 1-imidazolidinylcarbonyl, piperidinocarbonyl, 1-piperazinylcarbonyl, morpholinocarbonyl, thiomorpholinocarbonyl or the like.

The above "N-containing heterocycliccarbonyl" may optionally be substituted with a lower alkyl group as exemplified before.

Preferable examples of "N-containing heterocyclic-carbonyl substituted with lower alkyl" may be 3-methylpiperidinocarbonyl, 4-methylpiperidinocarbonyl, 4-methylpiperazin-1-ylcarbonyl, 2-ethylmorpholinocarbonyl, 2-isopropylthiomorpholin-4-ylcarbonyl, or the like.

Preferable examples of "ureido substituted with lower alkylamino(lower)alkyl" may be 3-(methylaminomethyl)ureido, 3-(dimethylaminomethyl)ureido, 3-(dimethylaminoethyl)ureido, 3-(diethylaminoethyl)ureido, 3-(N-methyl-N-ethylaminopropyl)ureido or the like.

Suitable "halo(lower)alkyl" may be the abovementioned lower alkyl substituted with halogen, or the like.

Suitable "N-containing heterocyclic group" formed by linkage of $R^1$ and $R^4$ may be saturated 5- or 6-membered heteromonocyclic group containing 1 or 2 nitrogen atom(s), for example, pyrrolidinyl, imidazolidinyl, piperidyl, piperazinyl or the like.

The above N-containing heterocyclic group may optionally be substituted with oxo and the abovementioned lower alkylamino(lower)alkyl.

Preferable examples of "N-containing heterocyclic group substituted with oxo and lower alkylamino(lower)alkyl" may be represented by the following formula:

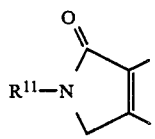

in which $R^{11}$ is as defined above.

Suitable "lower alkylene" may be a straight or branched one such as methylene, ethylene, trimethylene, methylethylene, tetramethylene, ethylethylene, propylene, pentamethylene, hexamethylene or the like.

Suitable "leaving group" may be an acid residue such as halogen [e.g. chlorine, bromine, fluorine and iodine], sulfonyloxy [e.g. mesyloxy, tosyloxy, phenylsulfonyloxy, etc.] or the like.

Suitable salts of the object compound [I] are conventional non-toxic pharmaceutically acceptable salts and may include a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], an organic acid salt [e.g. formate, acetate, fumarate, trifluoroacetate, maleate, tartrate, methanesulfonate, benzenesulfonate, toluenesulfonate, etc.], an inorganic acid salt [e.g. hydrochloride, hydrobromide, sulfate, phosphate, etc.], a salt with an amino acid [e.g. arginine salt, ornithine salt, etc.], and the like.

The processes for preparing the object compounds of the present invention are explained in more detail in the following.

PROCESS 1

The object compound [I] or its salt can be prepared by oxidizing a compound [II] or its salt.

Suitable salts of the compound [II] may be the same as those exemplified for the compound [I].

The oxidation reaction can be carried out by a conventional method which is applied for the transformation of an N-containing heterocyclic base to an aromatized N-containing heterocyclic compound, for example, by using an oxidizing agent such as manganese dioxide, lead tetraacetate, mercuric acetate, halogen [e.g. iodine, bromine, etc.], oxygen, hydrogen peroxide, nickel peroxide, sulfur powder, 2,3-dichloro-5,6-dicyano-1,4-benzoquinone, potassium permanganate, or the like.

The present reaction is usually carried out in a conventional solvent such as chloroform, methylene chloride, benzene, toluene, pyridine, ethyl acetate, acetone, or any other organic solvent which does not adversely affect the reaction.

The reaction temperature is not critical and the reaction is preferably carried out at ambient temperature or under warming to heating.

PROCESS 2

The object compound [Ia] or its salt can be prepared by reacting a compound [III] with a compound [IV] or its salt.

Suitable salts of the compounds [Ia] and [IV] may be the same as those exemplified for the compound [I].

The reaction can be carried out at ambient temperature or under warming to heating. The reaction can typically be conducted in the presence of a solvent such as aromatic solvent [e.g. benzene, toluene, xylene, etc.], halogenated hydrocarbon solvent [e.g. chloroform, carbon tetrachloride, methylene chloride, ethylene chloride, etc.], alcohol solvent [e.g. methanol, ethanol, propyl alcohol, isopropyl alcohol, butanol, etc.] or the like.

The reaction can optionally be accelerated in the presence of an acid [e.g. acetic acid, etc.], a base [e.g. pyridine, picoline, etc.] and the like.

PROCESS 3

The compound [Ic] or its salt can be prepared by subjecting a compound [Ib] or its salt to deesterification reaction.

Suitable salts of the compound [Ib] may be an acid addition salt as exemplified for the compound [I].

Suitable salts of the compound [Ic] may be the same as those exemplified for the compound [I].

Deesterification reaction is carried out in a conventional manner which is conventionally applied to a cleavage of a so-called ester bond into the carboxy function, and is preferably carried out, for example, by a basic hydrolysis, i.e. in the presence of a base such as an alkali metal hydroxide, carbonate or bicarbonate [e.g. sodium hydroxide, potassium hydroxide, sodium carbonate, potassium carbonate, sodium bicarbonate, etc.] or by an acidic hydrolysis in the presence of an inorganic acid [e.g. hydrochloric acid, sulfuric acid, etc.] or an organic acid [e.g. formic acid, acetic acid, trifluoroacetic acid, p-toluenesulfonic acid, etc.], or an acidic ion-exchange resin.

The reaction may preferably be carried out in a suitable conventional solvent such as water, acetone, alcohol [e.g. methanol, ethanol, etc. , N,N-dimethylformamide, or a mixture thereof, or the like.

The reaction temperature is not critical, and the reaction is usually carried out at ambient temperature or under warming to heating.

PROCESS 4

The object compound [Ie] or its salt can be prepared by reacting a compound [Ic] or its reactive derivative at the carboxy group or a salt thereof with a compound [V] or its salt.

Suitable salts of the compound [Ic] may be the same as those exemplified for the compound [I].

Suitable salts of the compounds [Ie] and [V] may be acid addition salt as exemplified for the compound [I].

As suitable said reactive derivatives at the carboxy group, there may be mentioned acid halides, acid anhydrides, active amides and esters. Suitable examples are acid halides such as acid chloride and acid bromide, mixed acid anhydrides with various acids [e.g. substituted phosphoric acid such as dialkyl phosphoric acid, sulfuric acid, aliphatic carboxylic acid, aromatic carboxylic acid, etc.], symmetric acid anhydrides, active amides with various imidazoles, and esters such as lower alkyl ester [e.g. methyl ester, ethyl ester, etc.], cyanomethyl ester, methoxymethyl ester, p-nitrophenyl ester, 2,4-dinitrophenyl ester, pentachlorophenyl ester, phenylazophenyl ester, carboxymethylthio ester and N-hydroxysuccinimide ester.

The reaction is usually carried out in a conventional solvent, such as methylene chloride, chloroform, alcohol [e.g. methanol, ethanol, etc.], benzene, toluene, pyridine, diethyl ether, dioxane, tetrahydrofuran, acetone, acetonitrile, ethyl acetate, N,N-dimethylformamide or any other organic solvent which does not adversely affect the reaction. In case that the compound [V] is liquid, it can also be used as a solvent. In case that the compound [Ic] is used in the free acid form or salt form, it is preferable to carry out the reaction in the presence of a conventional condensing agent such as N,N'-dicyclohexylcarbodiimide, phosphoryl chloride, phosphorus trichloride, thionyl chloride, oxalyl chloride, lower alkyl haloformate [e.g. ethyl chloroformate, isopropyl chloroformate, etc.], so-called Vilsmeier reagent prepared by the reaction of N,N-dimethylformamide with thionyl chloride, phosgene, trichloromethyl chloroformate, phosphoryl chloride, etc., or the like.

The reaction temperature is not critical and the reaction can be carried out under cooling, at ambient temperature, or under heating.

This reaction can typically be conducted in the presence or absence of an acceleralor such as base.

Suitable base may include a tertiary amine [e.g. triethylamine, pyridine, N,N-dimethylaniline, etc.], an alkali metal hydroxide [e.g. sodium hydroxide, potassium hydroxide, etc.], an alkali metal carbonate [e.g. sodium carbonate, potassium carbonate, etc.], alkali metal bicarbonate [e.g. sodium bicarbonate, etc.], a salt of an organic acid [e.g. sodium acetate, etc.] and the like. In case that the base is liquid, the base can be used as a solvent.

PROCESS 5

The compound [If] or its salt can be prepared by subjecting a compound [Ic] or its salt to azidation reaction and then reacting the resultant product with a compound [V'] or its salt.

Suitable salts of the compounds [If] and [V'] may be an acid addition salt as exemplified for the compound [I].

(i) The first step:

The reaction of this step can be carried out by reacting a compound [Ic] or its salt with an azide compound such as sodium azide, diphenylphosphoryl azide or the like under warming to heating.

The reaction can be carried out in the presence of a solvent such as benzene, toluene, acetone, dioxane, diethyl ether or any other solvent which does not adversely influence the reaction. This reaction can optionally be accelerated in the presence of a base as exemplified in the Process 4.

The reaction product of the first step is an isocyanate having the following formula [VII] and it can be subjected to the following second step with or without isolation and/or purification.

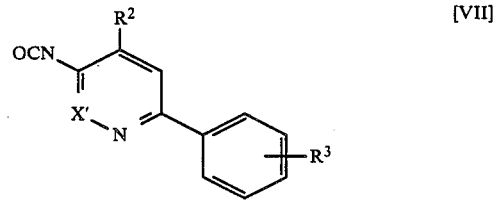

[wherein $R^2$, $R^3$ and $X'$ are each as defined above]

(ii) The second step:

The isocyanate compound [VII] or its salt obtained in the first step is then reacted with a compound [V'] or its salt to give a compound [If] or its salt.

Suitable salts of the isocyanate compound [VII] may be an acid addition salt as exemplified for the compound [I].

The reaction can be conducted in similar manners to those described in the Process 4 by referring to the reaction temperature, solvent and accelerator.

PROCESS 6

The compound [Ig] or its salt can be prepared by reducing a compound [Id] or its salt.

Suitable salts of the compounds [Id] and [Ig] may be the same as those exemplified for the compound [I].

The reduction can be carried out by a conventional method, for instance, by chemical reduction using a reducing agent.

Preferred examples of the reducing agents to be used in the chemical reduction may include lithium aluminum hydride, diisobutyl aluminum hydride, diborane, sodium borohydride and the like.

The reaction is usually carried out in a solvent such as water, diethyl ether, alcohol [e.g. methanol, ethanol, etc.], tetrahydrofuran, toluene, methylene chloride, or any other solvent which does not adversely affect the reaction, or a mixture thereof.

The reaction temperature is not critical, and the reaction is preferably carried out under cooling, at ambient temperature or under warming.

PROCESS 7

The object compound [Ii] or its salt can be prepared by halogenating a compound [Ih] or its salt.

Suitable salts of the compound [Ih] may be the same as those exemplified for the compound [I].

Suitable salts of the compound [Ii] may be an acid addition salt as exemplified for the compound [I].

Suitable examples of the halogenating agent to be used in this process may include a conventional ones such as phosphorus oxyhalide [e.g. phosphorus oxybromide, phosphorus oxychloride, etc.], phosphorus pentahalide [e.g. phosphorus pentabromide, phosphorus pentachloride, phosphorus pentafluoride, etc.], phosphorus trihalide [e.g. phosphorus tribromide, phosphorus trichloride, phosphorus trifluoride, etc.], thionyl halide [e.g. thionyl chloride, thionyl bromide, etc.], triphenylphosphine dihalide [e.g. triphenylphosphine dichloride, triphenylphosphine dibromide, etc.], or the like.

This reaction is usually carried out in a conventional solvent such as methylene chloride, chloroform, carbon tetrachloride, benzene, tetrahydrofuran, dimethylformamide, dimethyl sulfoxide or any other organic solvent which does not adversely influence the reaction or a mixture thereof. In case that the halogenating agent is liquid, it can be used as a solvent.

The reaction temperature is not critical, and the reaction can be carried out under cooling to heating.

PROCESS 8

The object compound [Ij] or its salt can be prepared by reacting a compound [Ii'] or its salt with a compound [V''] or its salt.

Suitable salts of the compounds [Ii'], [Ij] and [V''] may be an acid addition salt as exemplified for the compound [I].

This reaction is usually carried out in a conventional solvent such as water, an alcohol [e.g. methanol, ethanol, isopropyl alcohol, etc.], dioxane, tetrahydrofuran, N,N-dimethylformamide, methylene chloride, chloroform, tetrachloromethane, or any other conventional solvent which does not adversely affect this reaction, or a mixture thereof.

The reaction is carried out at ambient temperature, under warming or under heating, although the reaction temperature is not critical.

This reaction can also be conducted in the presence of an inorganic base, for example an alkali metal hydroxide such as sodium hydroxide or potassium hydroxide, or an alkali metal carbonate or hydrogen carbonate such as sodium carbonate, potassium carbonate, sodium hydrogen carbonate or potassium hydrogen carbonate, or in the presence of an organic base, for example, a tertiary amine such as triethylamine, pyridine or N,N-dimethylaniline.

This reaction can also be performed in the presence of an alkali metal halide such as sodium iodide or potassium iodide.

PROCESS 9

The object compound [Il] or its salt can be prepared by halogenating a compound [Ik] or its salt.

Suitable salts of the compounds [Ik] and [Il] may be the same as those exemplified for the compound [I].

This halogenation reaction is carried out in the presence of halogenating agent such as halogen [e.g. chlorine, bromine, etc.], N-halosuccinimide [e.g. N-bromosuccinimide, N-chlorosuccinimide, etc.], ω-tribromcacetophenone, trichloromethanesulfonyl chloride, trichloromethanesulfonyl bromide, aluminum chloride, aluminum bromide, or the like. In case that N-halosuccinimide is used as halogenating agent, this reaction is preferably carried out in the presence of benzoyl peroxide.

The reaction is usually carried out in a conventional solvent such as tetrachloromethane, benzene, acetic acid, tetrahydrofuran, or the like.

The reaction temperature is not critical, and the reaction is usually carried out under cooling to heating.

PROCESS 10

The object compound [Im] or its salt can be prepared by reacting a compound [Il'] or its salt with a compound [VI] or its salt.

Suitable salts of the compound [Il'] may be the same as those exemplified for the compound [I].

Suitable salts of the compounds [Im] and [VI] may be an acid addition salt as exemplified for the compound [I].

This reaction can be carried out in substantially the same manner as that of Process 8, and therefore the reaction mode and reaction conditions of this reaction can be referred to those as explained in Process 8.

Among the starting compounds in the above processes, some of them are new and can be prepared by processes as illustrated in the following reaction schemes.

Process A

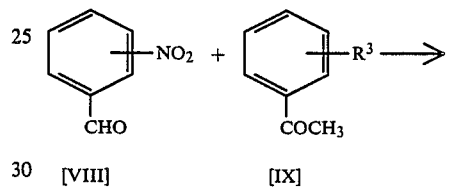

[VIII]    [IX]

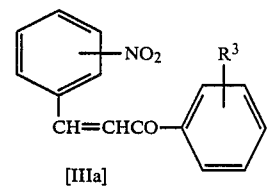

[IIIa]

Process B

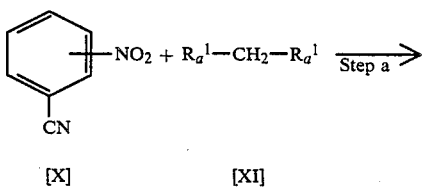

[X]    [XI]

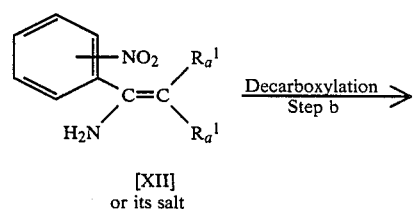

[XII]
or its salt

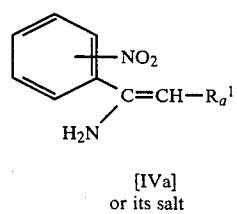

[IVa]
or its salt

Process C

-continued

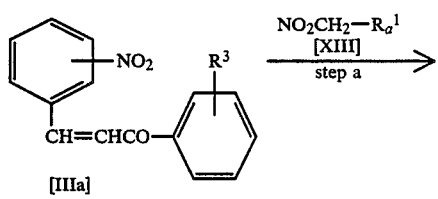

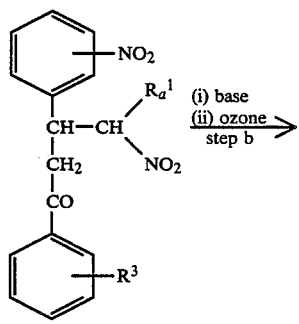

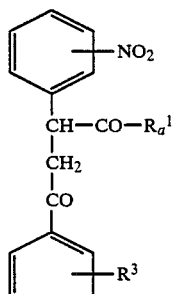

Process D

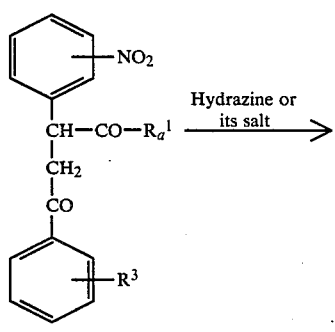

-continued

[IIa]
or its salt

Process E

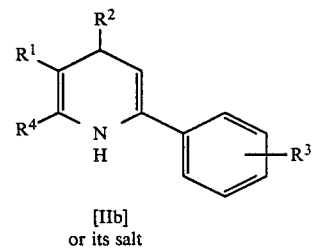

[III]

[IV]
or its salt

[IIb]
or its salt wherein $R^1$, $R^2$, $R^3$, $R^4$ and $R^1_a$ are each as defined above.

The processes for preparing the starting compounds are explained in detail in the following.

Process A

The compound [IIIa] can be prepared by reacting a compound [VIII] with a compound [IX].

The reaction can be conducted according to a similar manner to that of the synthesis of some of the compound [Ia] as stated above (Process 2). Therefore, some of the compound [Ia] or its salt can also be prepared by reacting a compound IV] or its salt with a compound [VIII] and a compound [IX] in one batch.

Process B

Step a

The compound [XII] or its salt can be prepared by reacting a compound [X] with a compound [XI].

Suitable salts of the compound [XII] may be an acid addition salt as exemplified for the compound [I].

This reaction is usually carried out in a solvent such as dioxane, tetrahydrofuran, benzene, chloroform, methylene chloride, N,N-dimethylformamide or any other organic solvent which does not adversely influence the reaction.

Further, this reaction can be carried out in the presence of a base such as an alkali metal [e.g. sodium, potassium, etc.], an alkaline earth metal [e.g. magnesium, calcium, etc.], the hydride or hydroxide thereof, alkali metal alkoxide [e.g. sodium methoxide, sodium ethoxide, potassium tert-butoxide, etc.], trialkylamine [e.g. trimethylamine, triethylamine, etc.], picoline, 1,5-diazabicyclo[4.3.0] non-5-ene, 1,4-diazabicyclo-[2.2.2]octane, 1,8-diazabicyclo[5.4.0]undec-7-ene, etc. or in the presence of a Lewis acid such as aluminum halide [e.g. aluminum chloride, aluminum bromide, etc.], boron trihalide [e.g. boron trichloride, boron trifluoride, etc.], zinc halide [e.g. zinc chloride, etc.], stannic halide [e.g. stannic chloride, etc.], titanium halide [e.g. titanium tetrachloride, etc.]or the like, protonic acids such as hydrogen halide [e.g. hydrogen fluoride, etc.], sulfuric acid, polyphosphoric acid, etc.

The reaction temperature is not critical and the reaction is usually carried out under cooling to heating.

Step b

The compound [IVa] or its salt can be prepared by subjecting a compound [XII] or its salt to decarboxylation reaction.

Suitable salts of the compound [IVa] may be the same as those exemplified for the compound [XII].

This reaction is usually carried out in a conventional solvent such as water, an alcohol [e.g. methanol, ethanol, isopropyl alcohol, etc.], dioxane, tetrahydrofuran, N,N-dimethylformamide, methylene chloride, chloroform, tetrachloromethare, or any other conventional solvent which does not adversely affect this reaction, or a mixture thereof.

The reaction is usually carried out under heating, although the reaction temperature is not critical.

This reaction can also be conducted in the presence of an inorganic base, for example an alkali metal hydroxide such as sodium hydroxide or potassium hydroxide, or an alkali metal carbonate or hydrogen carbonate such as sodium carbonate, potassium carbonate, sodium hydrogen carbonate or potassium hydrogen carbonate, or in the presence of an organic base, for example a tertiary amine such as triethylamine, pyridine or N,N-dimethylaniline.

Process C

Step a

The compound [XIV] can be prepared by reacting a compound [IIIa] with a compound [XIII].

The reaction can typically be conducted in the presence of a base in a conventional solvent as exemplified in the Process 2 at ambient temperature or under warming to heating.

Suitable base may include an organic amine such as triethylamine, pyridine, piperidine, N,N-dimethylaniline or the like.

The reaction product [XIV] of the first step can be subjected to the following step b with or without isolation and/or purification.

Step b

The compound [XV] can be prepared by treating the compound [XIV] with a base (step b-i) followed by reaction with ozone (step b-ii).

(Step b-i)

Suitable base may include an alkali metal hydroxide, carbonate or bicarbonate [e.g. sodium hydroxide, potassium hydroxide, sodium carbonate, potassium carbonate, sodium bicarbonate, etc.], an alkali metal alkoxide [e.g. sodium methoxide, sodium ethoxide, etc.], butyl lithium, ammonia and the like. The reaction of the compound [XIV] and a base can typically be conducted in a conventional solvent as exemplified in the Process 2 under ice cooling to warming.

The reaction product of this step (step b-i) is a nitronate salt having the following formula [XVI] and it is subjected to the following step (step b-ii) with or without isolation and/or purification.

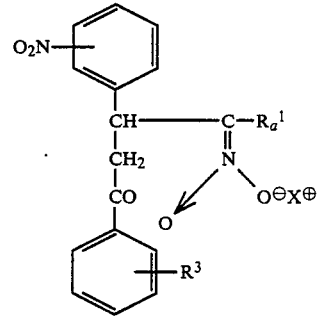

[XVI]

(wherein $R^3$ and $R^1_a$ are each as defined above and $X^\oplus$ is an alkali metal ion or ammonium ion).

(step b-ii)

The resultant product of the above step (step b-i) is treated with ozone in a conventional solvent as described in the above step (step b-i) to give a compound [XV]. The reaction is typically conducted by passing ozone gas into the reaction mixture containing the compound [XVI] under cooling preferably below $-70°$ C.

Process D

The compound [IIa] or its salt can be prepared by reacting a compound [XV] with hydrazine or its salt. Preferable examples of "hydrazine or its salt" may include hydrazine anhydrous, hydrazine hydrate, hydrazine dihydrochloride, hydrazine iodide, hyrazine sulfate, hydrazine tartrate and the like.

This reaction can be carried out in substantially the same manner as that of Process 2, and therefore the reaction mode and reaction conditions of this reaction can be referred to those as explained in Process 2.

Process E

The object compound [IIb] or its salt can be prepared by reacting a compound [III] with a compound [IV] or its salt.

This reaction can be carried out in substantially the same manner as that of Process 2, and therefore the reaction mode and reaction conditions of this reaction can be referred to those as explained in Process 2.

These reaction conditions stated in the above Processes may vary according to the kinds of reactants, solvents and/or other agents.

The compounds obtained by the above Processes can be separated and isolated from the reaction mixture and purified by methods commonly used for this purpose, for instance, extraction with suitable solvent, column chromatography, reprecipitation, recrystallization and so on.

It is to be noted that each of the object compound [I] and the starting compounds may include one or more stereoisomers due to asymmetric carbon atom(s) and/or carbon and carbon double bond [i.e. Z-isomer and E-isomer], and all of such isomers and a mixture thereof are included within the scope of this invention.

The N-containing heterocyclic compounds [I] and their salts of this invention have been found to be useful in the treatment of cerebrovascular diseases such as cerebral apoplexy [e.g. cerebral hemorrhage, cerebral infarction, transient cerebral ischemic attack] or the like.

The object compound [I] and their salts of this invention can be used in a form of a conventional pharmaceutical preparation, for example, in solid, semisolid or liquid form, which contains an active substance of this invention in admixture with an organic or inorganic carrier or excipient suitable for external, oral or parenteral applications. The active ingredient may be compounded, for example, with the usual non-toxic, pharmaceutically acceptable carriers for tablets, pellets, capsules, patch, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing thickening and coloring agents and perfumes may be used. The pharmaceutical compositions can also contain preservative or bacteriostatic agents to keep the active ingredient in the desired preparations stable in activity. The active object compound is included in the pharmaceutical composition in the amount sufficient to produce the desired therapeutic effect upon the process of condition of diseases.

While a dosage or therapeutically effective amount of the object compound [I] of this invention varies according to the age and conditions of each individual patient to be treated, a daily dose of about 0.1–100 mg/kg, preferably 1 to 50 mg/kg of the active ingredient may be generally given for treating diseases.

The pharmaceutical compositions of this invention comprises, as an active ingredient, the compound [I] or its salt in an amount of about 0.01 mg to about 500 mg, per dosage unit for oral and parenteral use.

For the purpose of showing utility of the object compound, [I], pharmacological test data thereof are illustrated in the following.

Test compounds:

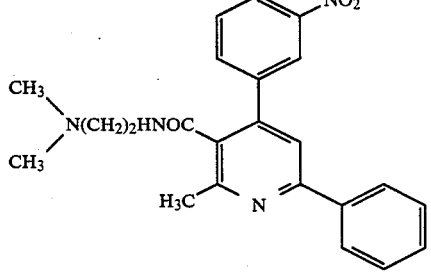

Example 8

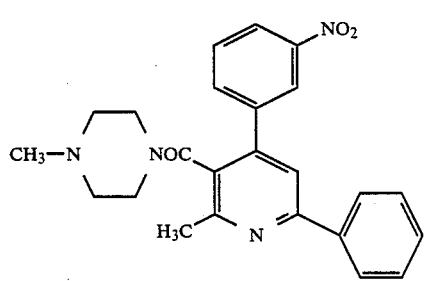

Example 9-(1)

Test compounds:

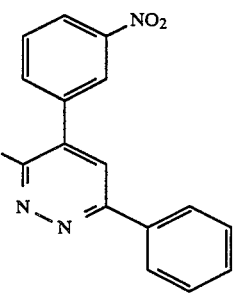

Example 13-(2)

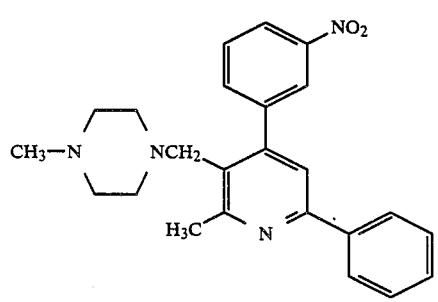

Example 20

.2HCl

Test 1. Effect on lipid peroxide production in rat brain mitochondria

Method:

Brain mitochondria from male Wistar rat was incubated with 100 $\mu$M ascorbic acid, 20 $\mu$M FeSO$_4$ and test drug for 1 hr at 37° C. Malondialdehyde formed in the incubation mixture was measured by the thiobarbituric acid method according to Shimada et al (Biochem. Biophys. Acta, 489; 163–172, 1977)

| Compounds | Results Inhibition % at $10^{-4}$ g/ml | at $10^{-5}$ g/ml |
|---|---|---|
| Example 8 | 75.3** | 40.1 |
| Example 9-(1) | — | 71.3** |

**: $P < 0.01$ compared with control

The compounds listed in the table inhibited significantly the malondialdehyde formation in rat brain mitochondria at the dose of $10^{-4}$ g/ml.

Test 2. Effect on survival time of mice subjected to anoxia (100% N$_2$)

Method:

A pair of male ICR mice with the same age was maintained in a close glass chamber in which circulated a current of nitrogen gas, and measured survival time.

One mouse was pretreated intraperitoneally with the test compound, and another with the vehicle 30 min. before the experiment.

Results

| Compounds | n | Survival time (sec) | | | |
|---|---|---|---|---|---|
| | | Control | 10 mg/kg | Control | 32 mg/kg |
| Example 8 | 20 | 31.5 ± 1.1 | 34.3 ± 1.0 | 31.0 ± 1.3 | 36.0 ± 1.1** |
| Example 13-(2) | 5 | 26.6 ± 0.7 | 30.2 ± 2.2 | 27.0 ± 1.3 | 37.4 ± 2.2** |
| Example 20 | 5 | 27.2 ± 1.1 | 28.4 ± 1.7 | 28.4 ± 1.0 | 37.4 ± 2.0** |

**: $P < 0.01$ compared with control

The following Preparations and Examples are given for the purpose of illustrating this invention.

Preparation 1

A mixture of 3-(3-nitrophenyl)-1-phenyl-2-propen-1-one (0.5 g), ethyl nitroacetate (0.29 g), piperidine (3 drops), dioxane (5 ml) and ethanol (5 ml) was refluxed for 2 hours. After allowing to cooling at ambient temperature, the reaction mixture was evaporated in vacuo. The residue was subjected to a column chromatography on silica gel (50 ml) eluting with benzene. The fractions containing the object compound were combined and concentrated under reduced pressure to give ethyl 2-nitro-3-(3-nitrophenyl)-5-oxo-5-phenylpentanoate (0.15 g).

mp: 78°–82° C. (recrystallized from ethanol)
IR (Nujol): 1750, 1683, 1565, 1538 cm$^{-1}$

| NMR (CDCl$_3$, δ): | 1.12 (t, J=7Hz) | } 3H, |
| --- | --- | --- |
| | 1.26 (t, J=7Hz) | |
| | 3.5–4.8 (2H, m), | |
| | 4.12 (q, J=7Hz) | } 2H, |
| | 4.27 (q, J=7Hz) | |
| | 4.4–4.8 (1H, m), | |
| | 5.57 (d, J=6Hz) | } 1H, |
| | 5.66 (d, J=6Hz) | |
| | 7.25–8.3 (9H, m) | |

Preparation 2

To a solution of ethyl 2-nitro-3-(3-nitrophenyl)-5-oxo-5-phenylpentanoate (2 g) in a mixture of methanol (30 ml) and methylene chloride (30 ml) was added sodium methoxide (0.28 g) and stirred for 10 minutes at −20° C. to give the nitronate salt. The reaction mixture was then cooled to −60° C., and a stream of ozone-oxygen was passed through until the reaction mixture was light blue.

After 30 minutes, the reaction mixture was purged with a nitrogen stream to remove excess ozone, and was then treated with 1 ml of dimethyl sulfide at −60° C. and slowly allowed to come to room temperature. Then the reaction mixture was poured into a mixture of methylene chloride (50 ml) and water (50 ml) with stirring. The organic layer was separated, washed with saturated brine, dried over magnesium sulfate and evaporated in vacuo. The residue was recrystallized from ethanol to give -ethyl 2,5-dioxo-3-(3-nitrophenyl)-5-phenylpentanoate (1.57 g).

mp: 70°–71° C.
IR (Nujol): 1733, 1685, 1535 cm$^{-1}$
NMR (CDCl$_3$, δ): 1.37 (3H, t, J=7 Hz), 3.2–4.1 (2H, m), 4.30 (2H, q, J=7 Hz), 5.1–5.4 (1H, m), 7.3–8.3 (9H, m)
Mass: 356 (M+1)

Preparation 3

To a mixture of dimethyl malonate (100 g) and 3-nitrobenzonitrile (112 g) in 1,2-dichloroethane (500 ml) was added stannic chloride (177 g) at once with a syringe and refluxed for 1 hour with stirring. The white precipitates were collected by filtration, dissolved in a mixture of acetone (2 l) and water (2 l) and adjusted to pH 9.0 with 20% aqueous sodium hydroxide. The resulting white solid was filtered off, and the filtrate was extracted with methylene chloride (2 l). The extract was washed with saturated aqueous sodium chloride, dried over magnesium sulfate and evaporated in vacuo. The resulting precipitates were recrystallized from a mixture of diethyl ether and methylene chloride to give dimethyl (α-amino-3-nitrobenzylidene)malonate (139.5 g).

mp: 113°–115° C.
IR (Nujol): 3350, 3175, 1670 cm$^{-1}$
NMR (CDCl$_3$, δ): 3.38 (3H, s), 3.78 (3H, s), 7.6–7.8 (2H, m), 8.2–8.4 (2H, m)
Mass: 280 (M+)

Preparation 4

A mixture of dimethyl (α-amino-3-nitrobenzylidene)-malonate (120 g) and potassium hydroxide in a mixture of methanol (1.2 l) and water(120 ml) was refluxed for 8 hours. The reaction mixture was concentrated under reduced pressure to a volume of 200 ml. The resulting crystals were collected by filtration and recrystallized from methanol to give methyl 3-amino-3-(3-nitrophenyl)-acrylate (50.2 g).

mp: 97°–99° C.
IR (Nujol): 3500, 3325, 1680, 1660, 1615 cm$^{-1}$
NMR (CDCl$_3$, δ): 3.74 (3H, s), 5.02 (1H, s), 6.1–6.9 (2H, br), 7.5–8.5 (4H, m)
Mass: 222 (M+)
Elemental analysis: $C_{10}H_{10}N_2O_4$
Calcd.: C 54.05, H 4.54, N 12.61
Found: C 54.16, H 4.27, N 12.61

Preparation 5

A mixture of 3-(3-nitrophenyl)-1-phenyl-2-propen-1-one (2 g), ethyl 3-aminocrotonate (1.2 g) and n-butanol (20 ml) was refluxed for 6 hours. After allowing to cool at ambient temperature, the reaction mixture was evaporated in vacuo. The residue was subjected to a column chromatography on silica gel (150 ml) eluting with a mixture of benzene and ethyl acetate (30:1 V/V). The fractions containing the object compound were combined and concentrated under reduced pressure to give ethyl 1,4-dihydro-2-methyl-4-(3-nitrophenyl)-6-phenyl-3-pyridinecarboxylate (0.6 g).

mp: 141°–142° C. (recrystallized from diisopropyl ether)
IR (Nujol): 3375, 1675, 1638 cm$^{-1}$
NMR (CDCl$_3$, δ): 1.15 (3H, t, J=8 Hz), NMR (CDCl$_3$, δ): 1.15 (3H, t, J=8Hz),
2.43 (3H, s), 4.05 (2H, q, J=8Hz),
4.83 (1H, d, J=5.5Hz), 5.12 (d, J=5.5Hz)  ⎫
                       5.15 (d, J=5.5Hz)  ⎬ 1H,
5.80 (1H, br), 7.2–8.2  (9H, m)

Mass: 364 (M+)
Elemental analysis: C$_{21}$H$_{20}$N$_2$O$_4$
Calcd.: C 69.22, H 5.53, N 7.69
Found: C 69.19, H 5.44, N 7.59

Preparation 6

The following compounds were obtained according to a similar manner to that of Preparation 5.

(1) Ethyl 6-(4-chlorophenyl)-1,4-dihydro-2-methyl-4-(3-nitrophenyl)-3-pyridinecarboxylate (3.1 g) was obtained from 1-(4-chlorophenyl)-3-(3-nitrophenyl)-2-propen-1-one (40 g).
mp: 130°–131° C.
IR (Nujol): 3350, 1665, 1635 cm$^{-1}$
NMR (CDCl$_3$, δ): 1.13 (3H, t, J=7 Hz), 2.42 (3H, s), 4.02 2 (2H, q, J=7 Hz), 4.80 (1H, d, J=5.5 Hz), 5.10 (d, J=5.5 Hz) 1H, 5.80 (1H, br), 5.12 (d, J=5.5 Hz) 7.30 (4H, s), 7.40 (1H, dd, J=9 Hz, 9 Hz), 7.63 (1H, ddd, J=9 Hz, 2 Hz, 2 Hz), 8.00 (1H, ddd, J=9 Hz, 2 Hz, 2 Hz), 8.15 (1H, dd, J=2 Hz, 2 Hz)
Mass: 398, 400 (M+)
Elemental analysis: C$_{21}$H$_{19}$ClN$_2$O$_4$
Calcd.: C 63.24, H 4.80, N 7.02, Cl 8.89
Found: C 63.47, H 4.77, N 7.09, Cl 9.21

(2) Ethyl 1,4-dihydro-2-methyl-4-(4-nitrophenyl) 6-phenyl-3-pyridinecarboxylate (28.0 g) was obtained from 3-(4-nitrophenyl)-1-phenyl-2-propen-1-one (40 g).
mp: 109°–110° C.
IR (Nujol): 3330, 1640, 1608, 1515, 1350 cm$^{-1}$
NMR (CDCl$_3$, δ): 1.13 (3H, t, J=7 Hz), 2.41 (3H, s), 4.0 (2H, q, J=7 Hz), 4.78 (1H, d, J=6 Hz), 5.07 (1H, d, J=6 Hz), 7.33 (5H, s), 7.42 and 8.1 (total 4H, ABq, J=9 Hz)
Mass: 364 (M+)

Preparation 7

A mixture of ethyl 2,5-dioxo-3-(3-nitrophenyl)-5-phenylpentanoate (1.5 g) and hydrazine monohydrate (0.24 g) in ethanol (30 ml) was refluxed for 5.5 hours. After evaporating the solvent in vacuo, the residue was subjected to a column chromatography on silica gel (100 ml) eluting with a mixture of benzene and ethyl acetate (50:1 V/V). The fractions containing the object compound were combined and concentrated under reduced pressure to give ethyl 1,4-dihydro-4-(3-nitrophenyl)-6-phenyl-3-pyridazinecarboxylate (0.52 g).
mp: 133°–134° C.
IR (Nujol): 3300, 1710, 1535 cm$^{-1}$ NMR (CDCl$_3$, δ): 1.30 (3H, t, J=7Hz), 4.25 (2H, q, J=7Hz), 4.95 (1H, d, J=6Hz), 5.19 (d, J=6Hz) ⎫
                                              5.21 (d, J=6Hz) ⎬ 1H,
7.3–7.85 (7H, m), 7.95–8.25 (3H, m)

Mass: 351 (M+)

EXAMPLE 1

A mixture of methyl 3-amino-3-(3-nitrophenyl)-acrylate (45 g) and 1-phenyl-2-buten-1-one (44 g) in n-butanol (450 ml) was refluxed for 4 hours. After allowing to cool at ambient temperature, the reaction mixture was evaporated in vacuo. The residue was subjected to a column chromatography on silica gel (500 g) eluting with benzene. The fractions containing the object compound were combined and concentrated under reduced pressure to give methyl 4-methyl-2-(3-nitrophenyl)-6-phenyl-3-pyridinecarboxylate (4.10 g).
mp: 105°–106° C. (recrystallized from ethanol)
IR (Nujol): 1685 cm$^{-1}$
NMR (CDCl$_3$, δ): 2.52 (3H, s), 3.76 (3H, s), 7.4–7.75 (4H, m), 7.66 (1H, s), 7.9–8.4 (4H, m), 8.55–8.65 (1H, m)
Mass: 348 (M+)
Elemental analysis: C$_{20}$H$_{16}$N$_2$O$_4$
Calcd.: C 68.96, H 4.63, N 8.04
Found: C 69.15, H 4.42, N 8.01

EXAMPLE 2

To a solution of ethyl 1,4-dihydro-2-methyl-4-(3-nitrophenyl)-6-phenyl-3-pyridinecarboxylate (0.5 g) in chloroform (5 ml) was added activated manganese dioxide (2 g) and the mixture was refluxed for 1 hour with stirring vigorously. After allowing to cool to ambient temperature, manganese dioxide was filtered off and the filtrate was evaporated in vacuo. The residual precipitates were recrystallized from ethanol, washed with ethanol and dried in vacuo to give ethyl 2-methyl-4-(3-nitrophenyl)-6-phenyl-3-pyridinecarboxylate (0.25 g)
mp: 110°–112° C.
IR (Nujol): 1720, 1595, 1360 cm$^{-1}$
NMR (CDCl$_3$, δ): 1.10 (3H, t, J=7 Hz), 2.73 (3H, s), 4.17 (2H, q, J=7 Hz), 7.2–8.3 (10H, m)
Mass: 362 (M+)
Elemental analysis: C$_{21}$H$_{18}$N$_2$O$_4$
Calcd.: C 69.60, H 5.00, N 7.73
Found: C 69.90 H 4 97, N 7.48

EXAMPLE 3

The following compounds were obtained according to a similar manner to that of Example 2.

(1) Ethyl 2-methyl 4-(4-nitrophenyl)-6-phenyl-3-pyridinecarboxylate
mp: 120°–122° C.
IR (Nujol): 1722, 1583, 1550, 1522, 1352 cm$^{-1}$
NMR (CDCl$_3$, δ): 1.06 (3H, t, J=7 Hz), 2.73 (3H, s), 4.15 (2H, q, J=7 Hz), 7.35–7.73 (6H, m), 7.95–8.4 (4H, m)
Mass: 362 (M+)

(2) Ethyl 6-(4-chlorophenyl)-2-methyl-4-(3-nitrophenyl)-3-pyridinecarboxylate
mp: 128°–130° C.
IR (Nujol): 1725, 1590, 1540, 1358 cm$^{-1}$
NMR (CDCl$_3$, δ): 1.10 (3H, t, J=7 Hz), 2.73 (3H, s), 4.17 (2H, q, J=7 Hz), 7.43 and 7.97 (total 4H, ABq, J=9 Hz), 7.50 (1H, s), 7.55–7.85 (2H, m), 8.15–8.40 (2H, m)
Mass: 396, 398 (M+)

EXAMPLE 4

To a solution of ethyl 1,4-dihydro-4-(3-nitrophenyl)-6-phenyl-3-pyridazinecarboxylate (0.4 g) in chloroform (6 ml) was added activated manganese dioxide (2 g) and the mixture was refluxed for 30 minutes with stirring vigorously. After allowing to cool to ambient temperature, manganese dioxide was filtered off. The filtrate was evaporated in vacuo, and the residual precipitate was recrystallized from diethyl ether. The crystal was collected by filtration, washed with diethyl ether and dried in vacuo to give ethyl 4-(3-nitrophenyl)-6-phenyl-3-pyridazinecarboxylate (0.2 g).
mp: 121°-122° C.
IR (Nujol): 1738, 1530 cm$^{-1}$
NMR (CDCl$_3$, δ): 1.30 (3H, t, J=7 Hz), 4.38 (2H, q, J=7 Hz), 7.4-7.8 (5H, m), 7.88 (1H, s), 8.0-8.4 (4H, m)

EXAMPLE 5

A mixture of ethyl 2-methyl-4-(3-nitrophenyl)-6-phenyl-3-pyridinecarboxylate (4.6 g), aqueous potassium hydroxide (1.07 g in 200 ml water) and ethanol (92 ml) was refluxed for 6 hours. After allowing to cool to ambient temperature, the reaction mixture was washed with ethyl acetate 150 ml×2). The separated aqueous layer was adjusted to pH 3.0 with 10% hydrochloric acid. To this mixture was added acetic acid (40 ml) and stirred for 30 minutes under ice cooling. The resulting precipitates were collected by filtration, washed with water and dried in vacuo to give 2-methyl-4-(3-nitrophenyl)-6-phenyl-3-pyridinecarboxylic acid (1.98 g).
mp: 274°-276° C. (dec.)
IR (Nujol): 1710, 1600 cm$^{-1}$
NMR (CF$_3$COOD, δ): 3.20 (3H, s), 7.5-8.1 (8H, m), 8.23 (1H, s), 8.3-8.6 (2H, m)
Mass: 334 (M+)
Elemental analysis: C$_{19}$H$_{14}$N$_2$O$_4$.¼H$_2$O
Calcd.: C 67.35, H 4.31, N 8.27
Found: C 67.59, H 4.20, N 8.13

EXAMPLE 6

2-Methyl-4-(4-nitrophenyl)-6-phenyl-3-pyridinecarboxylic acid was obtained according to a similar manner to that of Example 5.
mp: 260°-263° C.
IR (Nujol): 1710, 1595, 1545, 1515, 1345 cm$^{-1}$
NMR (DMSO-d$_6$, δ): 2.65 (3H, s), 7.3-7.9 (6H, m), 8.05-8.5 (4H, m)
Mass: 334 (M+)

EXAMPLE 7

A mixture of methyl 4-methyl-2-(3-nitrophenyl)-6-phenyl-3-pyridinecarboxylate (4.08 g), aqueous sodium hydroxide (0.94 g in 10 ml water), dioxane (20 ml) and methanol (80 ml) was refluxed for 14 hours. After allowing to cool to ambient temperature, the reaction mixture was poured into a mixture of water (150 ml) and chloroform (100 ml). The separated aqueous layer was adjusted to pH 2.9 with 10% aqueous hydrochloric acid. To this mixture was added acetic acid (15 ml) and stirred for 30 minutes under ice cooling. The resulting precipitates were collected by filtration, washed with water and dried in vacuo to give 4-methyl-2-(3-nitrophenyl)-6-phenyl-3-pyridinecarboxylic acid (2.80 g).
mp: 191°-192° C.
IR (Nujol): 1690, 1530 cm$^{-1}$
NMR (DMSO-d$_6$, δ): 2.50 (3H, s , 7.4-7.6 (3H, m), 7.7-8.6 (7H, m)
Mass: 334 (M+)
Elemental analysis: C$_{19}$H$_{14}$N$_2$O$_4$
Calcd.: C 68.25, H 4.22, N 8.38
Found: C 67.92, H 3.97, N 8.24

EXAMPLE 8

To a mixture of 2-methyl-4-(3-nitrophenyl)-6-phenyl-3-pyridinecarboxylic acid (1.98 g), methylene chloride (20 ml) and N,N-dimethylformamide (4 ml) was added a solution of thionyl chloride (0.47 ml) in methylene chloride (2 ml) at 7° C. under ice cooling. After stirring for 2.5 hours at the same condition, a solution of 2-dimethylaminoethylamine (1.3 g), in methylene chloride (20 ml) was added thereto and stirred for 2 hours at the same temperature. After adding water (150 ml) and methylene chloride (150 ml) thereto, the mixture was adjusted to pH 9.0 with 10% aqueous sodium hydroxide. The organic layer was separated, washed successively with water and saturated brine, dried over magnesium sulfate and evaporated in vacuo. The residue was subjected to a column chromatography on alumina (70 g) and eluted with chloroform. The fractions containing the object compound were combined and concentrated under reduced pressure. The residue was recrystallized from diethyl ether to give 3-(2-dimethylaminoethylcarbamoyl)-2-methyl-4-(3-nitrophenyl)-6-phenylpyridine (0.88 g).
mp: 143°-145° C.
IR (Nujol): 3275, 1640 cm$^{-1}$
NMR (CDCl$_3$, δ): 2.01 (6H, s), 2.17 (2H, t, J=6 Hz), 2.73 (3H, s), 3.27 (2H, td, J=6 Hz, 6 Hz), 6.27 (1H, br), 7.3-8.4 (10H, m)
Mass: 404 (M+)
Elemental analysis: C$_{23}$H$_{24}$N$_4$O$_3$
Calcd.: C 68.30, H 5.98, N 13.85
Found: C 68.26, H 5.86, N 14.10

EXAMPLE 9

The following compounds were obtained according to a similar manner to that of Example 8.

(1) 2-Methyl-3-(4-methylpiperazin-1-ylcarbonyl)-4-(3-nitrophenyl)-6-phenylpyridine
mp: 169°-172° C.
IR (Nujol): 1628, 1535, 1350 cm$^{-1}$
NMR (CDCl$_3$, δ): 1.6-2.4 (4H, m) 2.17 (3H, s), 2.67 (3H, s), 2.8-3.2 (2H, m), 3.4-3.8 (2H, m), 7.2-8.5 (10H, m)
Mass: 416 (M+)

(2) 3-(2-Morpholinoethylcarbamoyl)-2-methyl-4-(3-nitrophenyl)-6-phenylpyridine
mp: 137-139° C.
IR (Nujol): 3180, 1620, 1560, 1520, 1355 cm$^{-1}$
NMR (CDCl$_3$, δ): 2.15-2.4 (6H, m), 2.74 (3H, s), 3.2-3.7 (6H, m), 6.16 (1H, br), 7.4-7.75 (5H, m), 7.8-8.1 (3H, m), 8.15-8.43 (2H, m)
Mass: 446 (M+)

(3) According to a similar manner to that of Example 8, 2-methyl-4-(3-nitrophenyl)-6-phenyl-3-[2-(4-thiomorpholinyl)ethylcarbamoyl]pyridine was obtained and it was dissolved in a mixture of ethanol (20 ml) and fumaric acid (0.37 g) to give precipitates of fumarate thereof as crystal.
mp: 182°-184° C. (dec.)
IR (Nujol): 3300, 1665, 1590 cm$^{-1}$
NMR (DMSO-d$_6$, δ): 2.19 (2H, t, J=6 Hz), 2.50 (8H, s), 2.56 (3H, s), 3.15 (2H, td, J=6 Hz, 6 Hz), 6.57 (2H, s), 7.0-8.5 (13H, m)
Mass: 462 (M$^{30}$ of the free)

(4) According to a similar manner to that of the above (3), 3-(2-dimethylaminoethylcarbamoyl)-2-methyl-4-(4-nitrophenyl)-6-phenylpyridine fumarate was obtained.
mp: 185°-187° C.
IR (Nujol): 3450, 1710, 1660, 1350 cm$^{-1}$
NMR (DMSO-d$_6$, δ): 2.23 (6H, s), 2.3-2.5 (2H, m), 2.61 (3H, s), 3.25 (2H, q.like, J=6 Hz), 6.56 (2H, s), 7.3-7.9 (4H, m), 7.79 and 8.32 (total 4H, ABq, J=8 Hz), 8.0-8.2 (2H, m), 8.51 (1H, br)

EXAMPLE 10

To a mixture of 4-methyl-2-(3-nitrophenyl)-6-phenyl-3-pyridinecarboxylic acid (1.4 g), methylene chloride (14 ml) and N,N-dimethylformamide (2.8 ml) was added a solution of thionyl chloride (0.33 ml) in methylene chloride (3 ml) at 7° C. under ice cooling. After stirring for 2 hours at the same condition, a solution of 1-methylpiperazine (1.05 g) in methylene chloride (7 ml) was added thereto and the mixture was stirred for 2 hours at the same temperature. After adding water (100 ml) and methylene chloride (50 ml) thereto, the mixture was adjusted to pH 8.5 with 10% aqueous sodium hydroxide. The organic layer was separated, washed successively with water and saturated brine, dried over magnesium sulfate and evaporated in vacuo. The residue was recrystallized from a mixture of ethanol and diethyl ether to give 4-methyl-3-(4-methylpiperazin-1-ylcarbonyl)-2-(3-nitrophenyl)-6-phenylpyridine (0.97 g).

mp: 127°-129° C.
IR (Nujol): 1625, 1520 cm$^{-1}$
NMR (CDCl$_3$, δ): 1.5-3.8 (8H, m), 2.15 (3H, s), 2.45 (3H, s), 7.35-7.7 (4H, m), 7.67 (1H, s), 7.9-8.35 (4H, m), 8.65-8.80 (1H, m)
Mass: 416 (M+)
Elemental analysis: C$_{24}$H$_{24}$N$_4$O$_3$
Calcd.: C 69.21, H 5.81, N 13.45
Found: C 69.42, H 5.38, N 13.41

EXAMPLE 11

4-Methyl-3-(2-morpholinoethylcarbamoyl)-2-(3-nitrophenyl)-6-phenylpyridine was obtained according to a similar manner to that of Example 10.

mp: 147°-148° C.
IR (Nujol): 3280, 1625, 1525 cm$^{-1}$
NMR (CDCl$_3$, δ): 2.1-2.4 (6H, m), 2.51 (3H, s), 3.2-3.7 (6H, m), 6.20 (1H, br), 7.35-7.70 (5H, m), 7.90-8.35 (4H, m), 8.65-8.80 (1H, m)
Mass: 446 (M+)
Elemental analysis: C$_{25}$H$_{26}$N$_4$O$_4$
Calcd.: C 67.25, H 5.87, N 12.55
Found: C 67.23, H 5.82, N 12.52

EXAMPLE 12

A mixture of ethyl 4-(3-nitrophenyl)-6-phenyl-3-pyridazinecarboxylate (1.0 g) and 2-dimethylaminoethylamine (0.75 g) was heated for 30 minutes at 90° C. with stirring. After allowing to cool at ambient temperature, the resulting precipitates were collected by filtration, recrystallized from diethyl ether to give 3-(2-dimethylaminoethylcarbamoyl)-4-(3-nitrophenyl)-6-phenylpyridazine (1.04 g).

mp: 157°-158° C.
IR (Nujol): 1658, 1590, 1535 cm$^{-1}$
NMR (CDCl$_3$, δ): 2.28 (6H, s), 2.53 (2H, t, J=6 Hz), 3.50 (2H, t d, J=6 Hz, 6 Hz), 7.35-7.75 (5H, m), 7.81 (1H, s), 7.95-8.40 (4H, m), 8.45 (1H, t, J=6 Hz)
Mass: 391 (M+)

EXAMPLE 13

The following compounds were obtained according to a similar manner to that of Example 12.

(1) 3-(2-Morpholinoethylcarbamoyl)-4-(3-nitrophenyl)-6-phenylpyridazine mp: 134°-135° C.
IR (Nujol): 3280, 1640, 1535 cm$^{-1}$
NMR (CDCl$_3$, δ): 2.35-2.65 (4H, m), 2.60 (2H, t, J=6 Hz), 3.53 (2H, t d, J=6 Hz, 6 Hz), 3.6-3.85 (4H, m), 7.4-7.75 (5H, m), 7.81 (1H, s), 8.0-8.4 (4H, m), 8.43 (1H, t, J=6 Hz)
Mass: 433 (M+)
Elemental analysis: C$_{23}$H$_{23}$N$_5$O$_4$
Calcd.: C 63.73, H 5.35, N 16.16
Found: C 63.54, H 5.21, N 16.08

(2) 3-(4-Methylpiperazin-1-ylcarbonyl)-4-(3-nitrophenyl)-6-phenylpyridazine mp: 180°-181° C.
IR (Nujol): 1635, 1545, 1353 cm$^{-1}$
NMR (CDCl$_3$, δ): 2.33 (3H, s), 2.40 (2H, t, J=5.5 Hz), 2.46 (2H, t, J=5.5 Hz), 3.50 (2H, t, J=5.5 Hz), 3.80 (2H, t, J=5.5 Hz), 7.4-7.65 (3H, m), 7.76 (1H, dd, J=9 Hz, 9 Hz), 7.87 (1H, ddd, J=9 Hz, 2 Hz, 2 Hz), 7.91 (1H, s), 8.0-8.2 (2H, m), 8.31 (1H, ddd, J=9 Hz, 2 Hz, 2 Hz), 8.35 (1H, dd, J=2 Hz, 2 Hz)
Mass: 403 (M+)
Elemental analysis: C$_{22}$H$_{21}$N$_5$O$_3$
Calcd.: C 65.50, H 5.25, N 17.36
Found: C 65.76, H 5.15, N 17.06

EXAMPLE 14

To a solution of ethyl 4-(3-nitrophenyl)-6-phenyl-3-pyridazinecarboxylate (1 g) in methylene chloride (10 ml) was added ammonia-methanol solution (60 ml) which was prepared by bubbling an ammonia gas (14 g) into methanol (120 ml), and the mixture was stirred for 24 hours at ambient temperature. After evaporating the solvent, the residue was recrystallized from methanol to give 4-(3-nitrophenyl)-6-phenyl-3-pyridazinecarboxamide (0.78 g).

mp: 115°-117° C. (dec.)
IR (Nujol): 3160, 1670 cm$^{-1}$
NMR (CDCl$_3$, δ): 7.5-8.5 (9H, m), 7.35 (1H, s)
Elemental analysis: C$_{17}$H$_{12}$N$_4$O$_3$
Calcd.: C63.74, H 3.78, N 17.49
Found: C 63.58, H 3.73, N 17.40

EXAMPLE 15

A mixture of 2-methyl-4-(3-nitrophenyl)-6-phenyl-3-pyridinecarboxylic acid (5 g), triethylamine (1.5 g) and diphenylphosphorylazide (4.1 g) in benzene (50 ml) was refluxed for 2 hours. To the reaction mixture was added 2-dimethylaminoethylamine (1.6 g) and the mixture was further refluxed for 2 hours. After allowing to cool at ambient temperature, the reaction mixture was poured into a mixture of ethyl acetate (100 ml) and water (100 ml). The reaction mixture was adjusted to pH 2.0 with 10% hydrochloric acid. The aqueous layer was separated, washed with methylene chloride (100 ml) and adjusted to pH 9.0 with 10% aqueous sodium hydroxide. The resulting precipitates were collected by filtration, washed with water and dried in vacuo to give 3-[3-(2-dimethylaminoethyl)ureido]-2-methyl-4-(3-nitrophenyl)-6-phenylpyridine (1.87 g).

mp: 159°-161° C.
IR (Nujol): 3300, 1628, 1535 cm$^{-1}$
NMR (CDCl$_3$, δ): 2.10 (6H, s), 2.30 (2H, t, J=6 Hz), 2.58 (3H, s), 3.13 (2H, t d, J=6 Hz, 5 Hz), 5.60 (1H, t, J=5 Hz), 7.2-8.4 (11H, m)
Mass: 419 (M+), 331

EXAMPLE 16

To a suspension of lithium aluminum hydride (0.32 g) in a mixture of dry tetrahydrofuran (4 ml) and diethyl ether (8 ml) was dropwise added a solution of ethyl 2-methyl-4-(3-nitrophenyl)-6-phenyl-3-pyridinecarboxylate (1 g) in dry tetrahydrofuran (4 ml) at −20° C. to −10° C. The excess lithium aluminum hydride was decomposed by a careful addition to ice water. Ethyl acetate (25 ml) was added thereto and the separated organic layer was washed with 10% sulfuric acid (15 ml), saturated aqueous sodium bicarbonate and aqueous sodium chloride successively and concentrated in vacuo. The residue was subjected to a column chromatography on silica gel eluting with chloroform. The fractions containing the desired compound were combined and evaporated in vacuo. The residue was crystallized from diethyl ether to give 3-hydroxymethyl-2-methyl-4-(3-nitrophenyl)-6-phenylpyridine (0.27 g).

mp: 209°–214° C.

IR (Nujol): 3200, 1720, 1590, 1520, 1350 cm$^{-1}$

NMR (CDCl$_3$+DMSO-d$_6$, δ): 2.81 (3H, s), 4.45 (2H, d, J=5 Hz), 4.84 (1H, t, J=5 Hz), 7.2–8.5 (10H, m)

EXAMPLE 17

To a solution of ethyl 4-(3-nitrophenyl)-6-phenyl-3-pyridazinecarboxylate (1 g) in a mixture of ethanol (10 ml) and tetrahydrofuran (10 ml) was added sodium borohydride (0.22 g) and the mixture was stirred for 3 hours at ambient temperature. Then the reaction mixture was poured into a mixture of ethyl acetate (100 ml) and water (50 ml) The organic layer was washed with saturated aqueous sodium chloride, dried over magnesium sulfate and evaporated in vacuo. The residue was subjected to a column chromatography on silica gel (50 g) and eluted with a mixture of benzene and ethyl acetate (5 1 V/V). The fractions containing the desired compound were combined and concentrated under reduced pressure. The residue was recrystallized from a mixture of ethanol and chloroform to give 3-hydroxymethyl-4-(3-nitrophenyl)-6-phenylpyridazine (0.19 g).

mp: 162°–164° C.

IR (Nujol): 3300, 1525, 1360 cm$^{-1}$

NMR (DMSO-d$_6$, δ): 4.75 (2H, d, J=6 Hz), 5.60 (1H, t, J=6 Hz), 7.35–7.60 (3H, m), 7.76 (1H, dd, J=8 Hz, 8 Hz), 8.0–8.4 (4H, m), 8.18 (1H, s), 8.58 (1H, dd, J=2 Hz, 2 Hz)

Elemental analysis: C$_{17}$H$_{13}$N$_3$O$_3$

Calcd.: C 66.44, H 4.26, N 13.68

Found: C 66.46, H 4.11, N 13.80

EXAMPLE 18

To a solution of phosphorus tribromide (0.93 g) in tetrahydrofuran (10 ml) was dropwise added a suspension of 3-hydroxymethyl-2-methyl-4-(3-nitrophenyl)-6-phenylpyridine (1.65 g) in tetrahydrofuran (10 ml) at 5°–10° C. After stirring for 1.5 hours at the same temperature, the reaction mixture was poured into ice-water (20 ml), adjusted to pH 9.5 with saturated aqueous potassium carbonate and extracted with ethyl acetate (40 ml). The organic layer was washed with saturated aqueous sodium chloride, dried over magnesium sulfate and evaporated in vacuo. The residue was subjected to a column chromatography on silica gel eluting with chloroform. The fractions containing the desired compound were combined and evaporated in vacuo to give 3-bromomethyl-2-methyl-4-(3-nitrophenyl)-6-phenylpyridine (0.49 g).

mp: 155°–157° C.

IR (Nujol): 1580, 1570, 1520, 1345 cm$^{-1}$

NMR (CDCl$_3$, δ): 2.82 (3H, s , 4.38 (2H, s), 7.2–8 5 (10H, m)

EXAMPLE 19

A solution of 3-hydroxymethyl-4-(3-nitrophenyl)-6-phenylpyridazine (0.86 g) in tetrahydrofuran (5 ml) was dropwise added to a solution of phosphorus tribromide (0.18 ml) in a mixture of tetrahydrofuran (10 ml) and benzene (5 ml) under ice cooling. After stirring for 4 hours at the same temperature, the reaction mixture was poured into ice-water (50 ml) adjusted to pH 9 with saturated aqueous potassium carbonate and extracted with ethyl acetate (50 ml). The separated organic layer was washed with saturated aqueous sodium chloride, dried over magnesium sulfate and evaporated in vacuo. The residue was subjected to a column chromatography on silica gel (50 g) and eluted with a mixture of chloroform and acetone (5:1 V/V). The fractions containing the desired compound were combined and concentrated under reduced pressure. The residue was recrystallized from diethyl ether to give 3-bromomethyl-4-(3-nitrophenyl)-6-phenylpyridazine (0.73 g).

mp: 139°–140° C. (dec.)

IR (Nujol): 1520, 1355 cm$^{-1}$

NMR (CDCl$_3$, δ): 4.77 (2H, s), 7.77 (1H, s), 7.4–8.6 (9H, m)

Mass: 368, 370 (M-1)

Elemental analysis: C$_{17}$H$_{12}$BrN$_3$O$_2$

Calcd.: C 55.16, H 3.27, N 11.35

Found: C 54.87, H 2.90, N 11.17

EXAMPLE 20

A mixture of 3-bromomethyl-2-methyl-4-(3-nitrophenyl)-6-phenylpyridine (0.45 g), 1-methylpiperazine (0.26 g) in isopropyl alcohol (4.5 ml) was refluxed for 1 hour. The reaction mixture was poured into ice-water (50 ml) and extracted with chloroform (60 ml). The organic layer was washed with saturated aqueous sodium chloride, dried over magnesium sulfate and evaporated in vacuo. The residue and hydrochloric acid (0.3 ml) were dissolved in ethanol (3 ml). The resulting crystal was collected by filtration and dried in vacuo to give 2-methyl-3-(4-methylpiperazin-1-ylmethyl)-4-(3-nitropheryl)-6-phenylpyridine dihydrochloride (0.55 g).

mp: 250° C. (dec.)

IR (Nujol): 1580, 1520, 1350 cm$^{-1}$

NMR (D$_2$O, δ): 2.1–3.65 (8H, m), 2.84 (3H, s), 2.99 (3H, s), 3.77 (2H, s), 7.5–8.0 (8H, m), 8.3–8.53 (2H, m)

Mass: 402 (M+)

Elemental analysis: C$_{24}$H$_{28}$N$_4$O$_2$Cl$_2$.1.5 H$_2$O

Calcd.: C 57.37, H 6.22, N 11.15, Cl 14.11

Found: C 57.20, H 6.20, N 11.05, Cl 14.49

EXAMPLE 21

A mixture of 3-bromomethyl-4-(3-nitrophenyl)-6-phenylpyridazine (0.6 g), 1-methylpiperazine (0.36 g) in isopropyl alcohol (6 ml) was refluxed for 30 minutes. After evaporating the solvent, the residue was dissolved in methylene chloride (50 ml), washed with saturated aqueous sodium chloride and dried over magnesium sulfate. The solvent was evaporated under reduced pressure, and the residue was subjected to a column chromatography on silica gel (50 g) and eluted with a mixture of chloroform and methanol (20:1 V/V). The fractions containing the desired compound were combined and concentrated under reduced pressure The residue was recrystallized from ethanol to give 3-(4-methylpiperazin-1-ylmethyl)-4-(3-nitrophenyl)-6-phenylpyridazine (0.32 g).

mp: 157°–159° C.

IR (Nujol): 1520, 1355 cm$^{-1}$

NMR (CDCl$_3$, δ): 2.27 (3H, s), 2.2–2.8 (8H, m) 3.76 (2H, s), 7.4–8.5 (8H, m), 7.80 (1H, s), 8.8–9.0 (1H, m)

Mass: 389 (M+)

Elemental analysis: C$_{22}$H$_{23}$N$_5$O$_2$

Calcd.: C 67.85, H 5.95, N 17.98

Found: C 67.98, H 5.67, N 17.92

EXAMPLE 22

A mixture of ethyl 2-methyl-4-(3-nitrophenyl)-6-phenyl-3-pyridinecarboxylate (5 g), N-bromosuccinimide (5.9 g) and benzoyl peroxide (0.1 g) in carbon tetrachloride (200 ml) was refluxed for 5 hours. The reaction mixture was poured into ice water (100 ml). The separated organic layer was washed with saturated aqueous sodium hydrogen carbonate and saturated aqueous sodium chloride successively, dried over magnesium sulfate and evaporated in vacuo. The residue was subjected to a column chromatography on silica gel eluting with a mixture of n-hexane and chloroform (1:2 V/V). The fractions containing the desired compound were combined and evaporated in vacuo to give ethyl 2-bromomethyl-4-(3-nitrophenyl)-6-phenyl-3-pyridinecarboxylate (2 g).

mp: 125°–128° C.

IR (Nujol): 1710, 1590, 1570, 1520, 1350 cm$^{-1}$

NMR (DMSO-d$_6$, δ): 1.0 (3H, t, J=7 Hz), 4.16 (2H, q, J=8 Hz), 4.88 (2H, s), 7.4–8.6 (10H, m)

EXAMPLE 23

A mixture of ethyl 2-bromomethyl-4-(3-nitrophenyl)-6-phenyl-3-pyridinecarboxylate (1.5 g) and 2-dimethylaminoethylamine (0.6 g) is isopropyl alcohol (15 ml) was refluxed for 1 hour. The reaction mixture was evaporated in vacuo and the residue was dissolved in a mixture of water (20 ml) and chloroform (40 ml). The organic layer was washed with water and dried over magnesium sulfate. The solvent was distilled off. The residue was subjected to a column chromatography on silica gel, eluting with a mixture of chloroform and methanol (50:1 V/V). The fractions containing the desired compound were combined and evaporated in vacuo. The crystalline residue was recrystallized from ethanol to give 6-(2-dimethylaminoethyl)-4-(3-nitrophenyl)-5-oxo-2-phenyl-5,7-dihydro-(6H)-pyrrolo[3,4-b]pyridine (0.49 g).

mp: 179°–181° C.

IR (Nujol): 1675, 1585, 1565, 1525, 1345 cm$^{-1}$

NMR (CDCl$_3$+DMSO-d$_6$, δ): 2.29 (6H, s), 2.6 (2H, t, J=6 Hz), 3.73 (2H, t, J=6 Hz), 4.64 (2H, s), 7.3–7.78 (5H, m), 7.9–8.35 (4H, m), 8.4–8.58 (1H, m)

Mass: 402 (M+)

Elemental analysis: C$_{23}$H$_{22}$N$_4$O$_3$·¼H$_2$O

Calcd.: C 67.88, H 5.57, N 13.77

Found: C 67.82, H 5.41, N 13.77

What we claim is:

1. A diphenylpyridiazine compound of the formula:

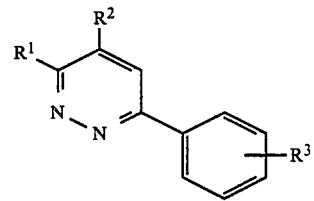

wherein R$^1$ is piperazinyl(lower)alkyl, carbamoyl substituted with piperazinyl(lower)alkyl, or piperazinylcarbonyl, in each of which a piperazinyl group may be substituted with lower alkyl, R$^2$ is phenyl substituted with nitro, and R$^3$ is hydrogen or halogen, or a pharmaceutically acceptable salt thereof.

2. A compound of claim 1, wherein R$^1$ is hydroxy(lower)-alkyl, halo(lower)alkyl, heterocyclic(lower)alkyl, carboxy, lower alkoxycarbonyl, carbamoyl, carbamoyl substituted with heterocyclic(lower)alkyl, carbamoyl substituted with lower alkylamino(lower)-alkyl, N-containing heterocyclicarbonyl substituted with lower alkyl, or ureido substituted with lower alkylamino(lower)alkyl;

R$^2$ is phenyl substituted with nitro, and

R$^4$ is lower alkyl or halo(lower)alkyl, or is taken together with R$^1$ to form a group of the formula:

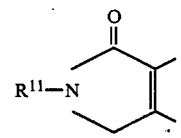

in which R$^{11}$ is lower alkylamino(lower)alkyl; or

R$^2$ is lower alkyl, and

R$^4$ is phenyl substituted with nitro.

3. A compound of claim 2, which is represented by the formula:

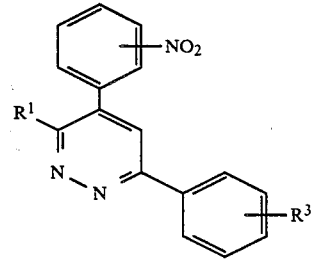

4. A compound of claim 1, which is 3-(4-methylpiperazin-1-ylcarbonyl)-4(3-nitrophenyl)-6-phenylpyridazine.

5. A cerebrovascular pharmaceutical composition comprising an effective amount of a compound of claim 1 in association with a pharmaceutically acceptable, substantially nontoxic carrier or excipient.

6. A method for the therapeutic treatment of cerebrovascular disease which comprises administering an effective amount of a compound of claim 1 to human beings or animals.

* * * * *